United States Patent [19]

Christensen et al.

[11] Patent Number: Plant 7,089

[45] Date of Patent: Jan. 2, 1990

[54] ROSE PLANT AROMIFI

[75] Inventors: Jack E. Christensen, Ontario; Thomas F. Carruth, Altadena, both of Calif.

[73] Assignee: Bear Creek Gardens, Inc., Medford, Oreg.

[21] Appl. No.: 276,424

[22] Filed: Nov. 23, 1988

[51] Int. Cl.[4] ..... A01H 5/00

[52] U.S. Cl. ..... Plt./7

[58] Field of Search ..... Plt. 7

*Primary Examiner*—Robert E. Bagwill

*Attorney, Agent, or Firm*—Majestic, Parsons, Siebert & Hsue

[57] ABSTRACT

A rose variety of the miniature class is provided that bears petals with a dark red front and white reverse, has vigorous upright growth with long strong stems, provides a good vase life and is better than average in resisting disease.

1 Drawing Sheet

SUMMARY OF THE INVENTION

The present invention relates to a new and distinct variety of rose plant of the miniature class, which was originated by me by crossing an unnamed seedling with the variety Arofiric.

The primary objective of this breeding was to develope a breeding line of a new rose variety of the miniature class which incorporates the high yield quality of miniature roses with the upright stems and high centered flower form of cut flowers. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Petals with a dark red front and a white reverse;
2. A dark glossy foliage;
3. Vigorous upright growing plants;
4. Relatively long stems;
5. A good vase life; and
6. Better than average disease resistance.

Asexual reproduction of this new variety by root cuttings, as performed at Somis, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which was been denominated "Aromifi". Throughout this specification, color names beginning with a small letter signify ordinary dictionary significance for the color, while color names beginning with a capital letter designate values based upon the R.H.S. Colour Chart of The Royal Horticultural Society of London, England.

Observations of the buds and flowers were made from specimens grown in a greenhouse at Somis, Calif. in January.

Flower

The blooming habit is continuous. The bud size is one and one-half inches long by one inch wide when the petals start to unfurl. The bud is long, which is average for its class, with a pointed top and a broad base. The bud color when sepals first divide is reddish purple in areas exposed to light, blending to a cream white near White Group 155A where covered by sepals at the base of the petal. When half blown, the upper side of the petals is a deep rich crimson red near Red Group 53A over most of the petal surface, with the basal third of the petals being a cream white near White Group 155A. The lower side of petals is a light pink near Red Group 55C blending to a rich cream white near White Group 155A along the margins of the petals. Approximately ninety-five percent of the petal reverse is near White Group 155A. The color of the outside of the sepals is near Green Group 143C. The color of the inside of the sepals is near Green Group 141C. The outside of the flower has a smooth surface with a few hairs evenly spread across the surface and the inside has a fine wooly tomentum. There are three foliaceous appendaged sepals which are modestly longer than average. There are two unappendaged sepals with a serrated edge and a hairy edge. All five sepals have stipitate glands on the edges. The receptacle color is near Green Group 143C with reddish casts where the sun hits. The receptacle has a large size for its class, a funnel shape, and a mostly smooth, slightly hairy bloom. The peduncle is long for its class and is stiff and erect. The peduncle has a bronzy color and a smooth surface with a few stipitate glands mostly at the basal end. The flowers open slightly faster than average for the class.

Bloom

Bloom size is large for the class, with an average open size of two and one-half inches, borne singly. The stems are strong and long for the class. When first open the bloom is high centered in form and as the bloom opens the petals curl and are reflexed outward. Under normal conditions there are 25 to 28 petals with 5 to 6 petaloids. The upper side of the petals is a rich red color between near Red Group 45A and near Red Group 46A. The reverse side of the petals is a white color near White Group 155D. The base of the petals is near White Group 155A. The petals are bicolored, between near Red Group 45A and near Red Group 46A and near White Group 155D. There are no variegations. At the end of the first day the red will fade to somewhere between near Red Group 45C and near Red Group 46C. By the third day, coloration is approximately the same as after the first day, except that along the petal margin there is an uneven fading resulting in small blotches of between near Red Group 43C and near Red Group 43D.

There is a slight tea fragrance. The petal texture is thick. The petal shape is somewhat round to slightly obovate. The petal form has heavily recurved tips with outward edges slightly quilled.

The petals have an imbricated arrangement. The petals persist and hang on the plant a fair amount of time and last for a long time as a cut flower.

Reproductive Parts

The anthers are many, yellow and of a large size for the class. The anthers are tucked or partly tucked in the calyx and are mixed with the petaloids. The filaments are white, the pollen is gold yellow. The styles are orangey red near Red Group 43C, and the stigmas are greenish white.

Plant

The plant has a bush form and is a tall, growing miniature with an upright habit. It displays a very vigorous but compact growth.

Foliage

The foliage is of a medium to large size for its class and is abundant in quantity. New foliage is a dark green near Green Group 137A with margins and veins that are reddish near Greyed-Purple Group 185A. Old foliage is a dark green near Green Group 137A. A normal mid-stem leave has five leaflets. The leaflets have an oval pointed shape with a glossy, smooth texture, and have single edge serrations. Petiole rachis is reddish, and petiole underside is smooth with prickles. Stipules are medium. The foliage has better than average resistance to mildew under normal growing conditions at Somis, Calif.

Wood

New wood is reddish and dark green color with a smooth bark. Old wood has a green color and smooth bark.

Prickles

There are few to an ordinary number of prickles on the main canes from the base for the class. There are an ordinary number of prickles on the laterals from the main canes. In form, the prickles are of long size for the class and are hooked slightly downward. The prickles are red colored when young. There are no small prickles on the main stalks or laterals.

Parentage

The seed parent was an unnamed seedling. The pollen parent was of the variety Arofiric.

Classification

Botanical is rosa hybrid. Commercial is miniature.

I claim:

1. A new and distinct variety of rose plant of the miniature class, characterized particularly as to novelty by a strong color contrast between the dark red petal front and white reverse, dark green, highly glossy foliage, an upright plant habit with strong straight stems, a good vase life and a better than average disease resistance, essentially as described and illustrated herein.

* * * * *

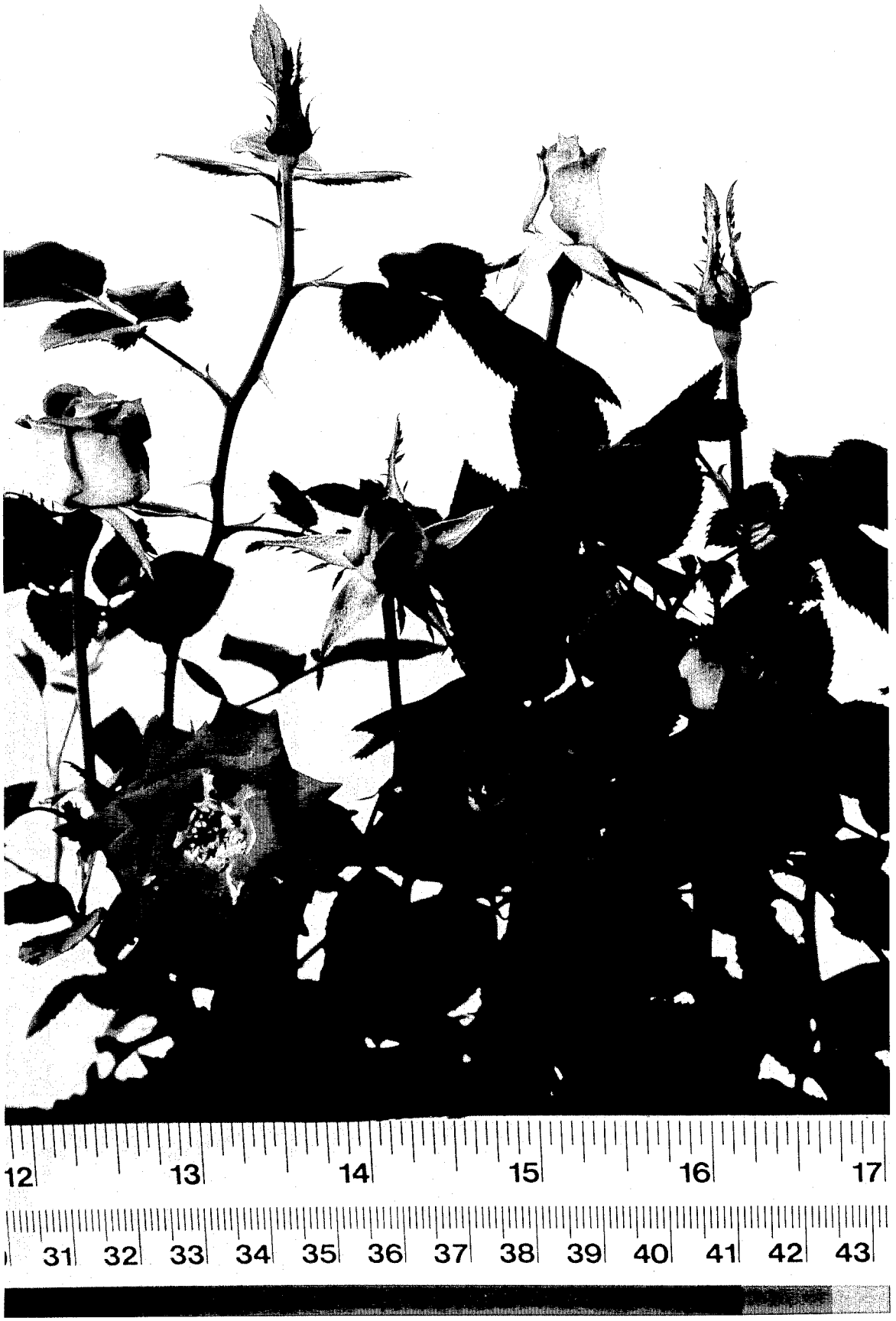
12
13
14
15
16
17
31
32
33
34
35
36
37
38
39
40
41
42
43